United States Patent
Gruba et al.

(10) Patent No.: US 10,465,318 B2
(45) Date of Patent: Nov. 5, 2019

(54) DEGRADABLE SCAFFOLDING FOR ELECTROSPINNING

(71) Applicants: Boston Scientific Scimed Inc., Maple Grove, MN (US); Mayo Foundation for Medical Education and Research, Rochester, MN (US)

(72) Inventors: Sarah M. Gruba, Vadnais Heights, MN (US); James P. Rohl, Prescott, WI (US); James A. Klos, Bay City, WI (US); Joseph B. Fitzgerald, Edina, MN (US)

(73) Assignees: Boston Scientific Scimed Inc, Maple Grove, MN (US); Mayo Foundation for Medical Education and research, Rochester, MN (US)

( * ) Notice: Subject to any disclaimer, the term of this patent is extended or adjusted under 35 U.S.C. 154(b) by 0 days.

(21) Appl. No.: 15/854,296

(22) Filed: Dec. 26, 2017

(65) Prior Publication Data
US 2018/0179680 A1    Jun. 28, 2018

Related U.S. Application Data

(60) Provisional application No. 62/439,313, filed on Dec. 27, 2016.

(51) Int. Cl.
*A61L 27/56*    (2006.01)
*D01D 5/00*    (2006.01)
(Continued)

(52) U.S. Cl.
CPC .............. *D04H 1/728* (2013.01); *A61L 27/34* (2013.01); *A61L 27/3895* (2013.01);
(Continued)

(58) Field of Classification Search
CPC .............................. A61L 27/56; D01D 5/0084
See application file for complete search history.

(56) References Cited

U.S. PATENT DOCUMENTS

| | | | |
|---|---|---|---|
| 5,157,929 A * | 10/1992 | Hotaling | A23G 3/28 426/250 |
| 5,861,023 A | 1/1999 | Vachon | |

(Continued)

FOREIGN PATENT DOCUMENTS

| | | |
|---|---|---|
| AU | 2012295332 B2 | 12/2014 |
| EP | 1646486 A2 | 4/2006 |

(Continued)

OTHER PUBLICATIONS

Datta, Jhunu and Nandi, Arun K. "Cocrystallization of Poly(Vinylidene Fluroide) and Vinylidene Fluoride-Tetrafluoro-ethylene Copolymer Blends: 3. Structural Study." Polymer 38(11):2719-2724, 1997.

(Continued)

*Primary Examiner* — Cachet I Proctor
(74) *Attorney, Agent, or Firm* — Faegre Baker Daniels, LLP

(57) ABSTRACT

Various aspects of the present disclosure are directed toward apparatuses, systems and methods that include a porous coating on a medical device. The porous coating may be formed by forming a scaffold along an exterior surface of the medical device to support the porous coating during application thereof and electrospinning a polymer to apply the porous coating on the scaffold.

18 Claims, 5 Drawing Sheets

(51) Int. Cl.
*D04H 1/728* (2012.01)
*A61L 27/58* (2006.01)
*C12N 5/00* (2006.01)
*A61L 27/38* (2006.01)
*A61L 27/34* (2006.01)

(52) U.S. Cl.
CPC .............. *A61L 27/56* (2013.01); *A61L 27/58* (2013.01); *C12N 5/0062* (2013.01); *D01D 5/0061* (2013.01); *A61L 2400/08* (2013.01); *A61L 2420/02* (2013.01)

(56) References Cited

U.S. PATENT DOCUMENTS

| | | | |
|---|---|---|---|
| 6,120,845 A * | 9/2000 | Pease | B05D 1/322 427/256 |
| 7,091,412 B2 | 8/2006 | Wang et al. | |
| 7,689,291 B2 | 3/2010 | Polkinghorne et al. | |
| 7,908,016 B2 | 3/2011 | Atanasoska et al. | |
| 8,070,718 B2 | 12/2011 | Weber et al. | |
| 8,903,506 B2 | 12/2014 | Arnholt et al. | |
| 8,965,531 B2 | 2/2015 | Arnholt et al. | |
| 9,011,754 B2 | 4/2015 | Leong et al. | |
| 9,415,206 B2 | 8/2016 | Arnholt et al. | |
| 9,855,415 B2 | 1/2018 | Delaney, Jr. et al. | |
| 2004/0175406 A1 | 9/2004 | Schwarz | |
| 2005/0149158 A1 | 7/2005 | Hunter et al. | |
| 2006/0159837 A1* | 7/2006 | Kaplan | A61L 27/227 427/2.1 |
| 2006/0264577 A1 | 11/2006 | Faust et al. | |
| 2007/0051531 A1 | 3/2007 | Borganonkar et al. | |
| 2007/0067882 A1 | 3/2007 | Atanasoska et al. | |
| 2007/0239245 A1 | 10/2007 | Borgaonkar et al. | |
| 2007/0255378 A1 | 11/2007 | Polkinghorne et al. | |
| 2008/0071338 A1 | 3/2008 | Jiang et al. | |
| 2009/0076530 A1 | 3/2009 | Fukutomi et al. | |
| 2009/0099441 A1 | 4/2009 | Giszter et al. | |
| 2009/0099634 A1 | 4/2009 | Atanasoska et al. | |
| 2009/0105796 A1 | 4/2009 | Atanasoska et al. | |
| 2009/0326077 A1 | 12/2009 | Desai et al. | |
| 2010/0023104 A1 | 1/2010 | Desai et al. | |
| 2010/0057197 A1 | 3/2010 | Weber et al. | |
| 2010/0069578 A1 | 3/2010 | Faust et al. | |
| 2010/0093093 A1* | 4/2010 | Leong | A61L 27/3847 435/396 |
| 2010/0179298 A1 | 7/2010 | Faust et al. | |
| 2010/0190254 A1 | 7/2010 | Chian et al. | |
| 2010/0241204 A1 | 9/2010 | Scheuermann | |
| 2010/0241208 A1 | 9/2010 | Pinchuk | |
| 2011/0021899 A1 | 1/2011 | Arps et al. | |
| 2011/0054580 A1 | 3/2011 | Desai et al. | |
| 2011/0054581 A1 | 3/2011 | Desai et al. | |
| 2011/0137389 A1 | 6/2011 | Polkinghorne et al. | |
| 2011/0196464 A1 | 8/2011 | Pinchuk | |
| 2013/0013040 A1 | 1/2013 | Desai et al. | |
| 2013/0041442 A1 | 2/2013 | Arnholt et al. | |
| 2013/0131765 A1 | 5/2013 | Polkinghorne et al. | |
| 2013/0231733 A1 | 9/2013 | Knisley et al. | |
| 2013/0238086 A1 | 9/2013 | Ballard et al. | |
| 2013/0268062 A1 | 10/2013 | Puckett et al. | |
| 2014/0141152 A1* | 5/2014 | Sostek | A61F 2/04 427/2.24 |
| 2014/0188212 A1* | 7/2014 | Haselby | D01D 5/003 623/1.15 |
| 2014/0324141 A1 | 10/2014 | Arnholt et al. | |
| 2015/0025608 A1 | 1/2015 | Delaney et al. | |
| 2015/0064142 A1* | 3/2015 | Green | A61L 27/18 424/93.7 |
| 2015/0088238 A1 | 3/2015 | Arnholt et al. | |
| 2015/0273110 A1* | 10/2015 | McClellan | A61L 27/34 427/2.24 |
| 2015/0343200 A1 | 12/2015 | Arnholt et al. | |
| 2017/0021160 A1 | 1/2017 | Delaney et al. | |

FOREIGN PATENT DOCUMENTS

| | | | |
|---|---|---|---|
| GB | 1527592 A | 10/1978 | |
| JP | H0411061 A | 1/1992 | |
| JP | 2001522654 A | 11/2001 | |
| JP | 2004119113 A | 4/2004 | |
| JP | 2005523116 A | 8/2005 | |
| JP | 2007154336 A | 6/2007 | |
| JP | 2008500104 A1 | 1/2008 | |
| JP | 2008515611 A | 5/2008 | |
| JP | 2008253297 A | 10/2008 | |
| JP | 2009000100 A | 1/2009 | |
| JP | 2009507577 A | 2/2009 | |
| JP | 2009531140 A | 9/2009 | |
| JP | 2009535182 A | 10/2009 | |
| JP | 2009540873 A | 11/2009 | |
| JP | 2010540105 A | 12/2010 | |
| SU | 132800 A | 1/1960 | |
| WO | WO1990008466 A1 | 8/1990 | |
| WO | WO2002089909 A1 | 11/2002 | |
| WO | WO2003045875 A1 | 6/2003 | |
| WO | WO2003101505 A1 | 12/2003 | |
| WO | WO2004041529 A1 | 5/2004 | |
| WO | WO2005032400 A2 | 4/2005 | |
| WO | WO2005039664 A2 | 5/2005 | |
| WO | WO2005065578 A2 | 7/2005 | |
| WO | WO2005079339 A2 | 9/2005 | |
| WO | WO2006020425 A1 | 2/2006 | |
| WO | 2006041767 A2 | 4/2006 | |
| WO | WO2006123340 A2 | 11/2006 | |
| WO | WO2007003199 A1 | 1/2007 | |
| WO | WO2007030722 A1 | 3/2007 | |
| WO | WO2007109007 A1 | 9/2007 | |
| WO | WO2007130900 A2 | 11/2007 | |
| WO | WO2008008266 A2 | 1/2008 | |
| WO | WO2008021020 A2 | 2/2008 | |
| WO | WO2008036460 A1 | 3/2008 | |
| WO | WO2008055038 A2 | 5/2008 | |
| WO | WO2008060333 A1 | 5/2008 | |
| WO | WO2008066538 A1 | 6/2008 | |
| WO | WO2008066914 A1 | 6/2008 | |
| WO | WO2008066912 A2 | 6/2008 | |
| WO | WO2009002984 A2 | 12/2008 | |
| WO | WO2009140381 A1 | 11/2009 | |
| WO | 2010053585 A1 | 5/2010 | |
| WO | 2010107967 A1 | 9/2010 | |
| WO | WO2010065484 A1 | 10/2010 | |
| WO | 2011017695 A1 | 2/2011 | |
| WO | 2011017698 A1 | 2/2011 | |
| WO | 2011028873 A2 | 3/2011 | |
| WO | 2013025465 A1 | 2/2013 | |
| WO | 2013112793 A1 | 8/2013 | |
| WO | 2013151778 A1 | 10/2013 | |
| WO | 2015134853 A1 | 9/2015 | |
| WO | WO-2015134853 A1 * | 9/2015 | ............ B33Y 10/00 |

OTHER PUBLICATIONS de Navarro, C. Urbina, et al. Contribucion Al Estudio De Los Factores Que Influyeron En Falla De Tuberias De PVDF. Acta Microscópica, 13(1):55-61, 2004. [English Abstract].

de Navarro, C. Urbina, et al. Relationship Between the Degradation of PVDF and the Presence of Crystalline Phases Alpha and the Mixed. CIASEM 201: 11th Inter American Congress on Microscopy, E.R.R.B.A.A.O. (UAY), Editor 2011, Merida Yucatan, Mexico.

de Obanos, Mercedes Perez, et al. "Corrosion Selectiva de las Estructuras Cristalinas del PVDF por Hidroxido de Sodio." Revista de la Facultad de Ingenieria de la U.C.V., 16(2):95-103, 2001, [English Abstract].

He, Fuan, et al. Preparation and Characterization of Electrospun Poly(Vinylidene Fluoride)/Poly(Methyl Methacrylate) Membrane. High Performance Polymers, 26(7):817-825, 2014.

Hong, Lingfei; Pan, Tingrui, "Photopatternable Superhydrophobic Nanocomposites for Microfabrication," Journal of Microelectromechanical Systems, vol. 19, No. 2, (Apr. 2010), pp. 246-253.

Huang, Zheng-Ming et al., "A review on polymer nanofibers by electrospinning and their applications in nanocomposites", Composites Science and Technology, No. 66, 2003, pp. 2223-2253.

(56) References Cited

OTHER PUBLICATIONS

International Preliminary Report on Patentability issued in PCT/US2016/043580, dated Feb. 8, 2018, 8 pages.
International Preliminary Report on Patentability, Chapter II, issued in PCT/US2012/050260, completed Oct. 28, 2013, 16 pages.
International Preliminary Report on Patentability, Chapter II, issued in PCT/US2012/065896, dated Dec. 18, 2013, 8 pages.
International Search Report and Written Opinion issued in PCT/US2012/050260, dated Dec. 7, 2012, 12 pages.
International Search Report and Written Opinion issued in PCT/US2012/065896, dated Feb. 20, 2013, 9 pages.
International Search Report and Written Opinion issued in PCT/US2016/043580, dated Oct. 13, 2016, 11 pages.
International Search Report and Written Opinion issued in PCT/US2017/068412, dated Apr. 18, 2018, 11 pages.
Jinglei Wu et al., "Enhancing cell infiltration of electrospun fibrous scaffolds in tissue regeneration", Bioactive Materials, vol. 1, No. 1, pp. 56-64, Jul. 26, 2016.
Lee, J. L., "Polymer Nanoengineering for Biomedical Applications", Annals of Biomedical Engineering,34(1), (2006), 75-88.
Liu, Xin, et al. "In Vivo Wound Healing and Antibacterial Performances of Electrospun Nanofibre Membranes." Journal of BioMedical Materials Research A, 94A(2):499-508, Aug. 2010.
Menini, Richard, et al., "Production of superhydrophobic polymer fibers with embedded particles using the electrospinning technique," Society of Chemical Industry, Polym Int 57, pp. 77-84 (2008). DOI: 10.1002/pi.
Ostwald, W. Studien Uber Die Bildung und Umwandlung Fester Korper—1. Abhandlung: Ubersattigung und Uberkaltung. Zietschrift f. physik. Chemie. XXII. Leipzig, Physiko-chemisches Laboratorium, Feb. 1897, pp. 289-330.
Ross, G. J., et al. Surface Modification of Poly(Vinylidene Fluoride) by Alkaline Treatment Part 2. Process Modification by the Use of Phase Transfer Catalysts. Polymer 42:403-413, 2001.
Ross, G. J., et al. Surface Modification of Poly(Vinylidene Fluoride) by Alkaline Treatment: 1. The Degradation Mechanism. Polymer 41:1685-1696, 2000.
Simonet, Marc; et al. "Ultraporous 3D Polymer Meshes by Low-Temperature Electrospinning: Use of Ice Crystals as a Removable Void Template." Polymer Engineering and Science, 2007, pp. 2020-2026.
Su, Ching-Iuan et al., "A Study of Hydrophobic Electrospun Membrane Applied in Seawater Desalination by Membrane Distillation," Fibers and Polymers (2012), vol. 13, No. 6, pp. 698-702. DOI 10.1007/s12221-012-0698-3.
Wikipedia. "Gel," [Online], Page last modified Jan. 1, 2017, retrieved from the Internet <https://en.wikipedia.org/wiki/Gel>, 7 pages.
Written Opinion of the International Preliminary Examining Authority issued in PCT/US2012/050260, dated Jul. 18, 2013, 7 pages.
Zhou, Tao; Yao, Yongyi; Xiang, Ruili; Wu, Yurong, "Formation and characterization of polytetrafluoroethylene nanofiber membranes for vacuum membrane distillation," Journal of Membrane Science 453 (2014), pp. 402-408. <www.elsevier.com/locate/memsci>.

\* cited by examiner

DEGRADABLE SCAFFOLDING FOR ELECTROSPINNING

CROSS-REFERENCE TO RELATED APPLICATION

This application claims priority to Provisional Application No. 62/439,313, filed Dec. 27, 2016, which is herein incorporated by reference in its entirety.

TECHNICAL FIELD

The present invention relates to medical devices and methods for a porous coating on a medical device. More specifically, the invention relates to devices and methods that include an electrospun material on a medical device.

BACKGROUND

An electrospun material arranged with a medical device may provide certain benefits to the function and/or operation of the medical devices upon which the electrospun material is arranged. Depending on the medical device, an electrospun material may provide a porous or partially porous membrane for drug, saline, and/or shock delivery; induce or inhibit cell growth; or be used for tissue engineering.

Coating medical devices may be challenging due a number of challenges that may cause uneven coatings, odd shapes, and/or the coating's inability to stretch after being spun. In addition, the medical device may be damaged by materials or chemicals used in the electrospinning process.

SUMMARY

In Example 1, a method of forming a porous coating on a medical device, the method including: forming a scaffold along an exterior surface of the medical device to support the porous coating during application thereof; electrospinning a polymer to apply the porous coating on the scaffold; and removing the scaffold from the medical device while maintaining the porous coating on the medical device.

In Example 2, the method of Example 1, wherein forming the scaffold comprises applying a degradable material along the exterior surface of the medical device.

In Example 3, the method of Example 2, wherein applying the degradable material comprises applying at least one of a degradable polymer and ice along the exterior surface of the medical device.

In Example 4, the method of Example 3, wherein applying the degradable material comprises applying at least one of a cellulose plant-based polymer, vinyl-based polymer, acrylic-based polymer, and a water-soluble polysaccharide.

In Example 5, the method of any of Examples 3-4, wherein applying the degradable material comprises applying at least one of Polyethylene glycol (PEG), Polyvinyl Pyrrolidone (PVP), polyacrylamide, Polyisobutylene polyurethane (PIB PUR), Polycaprolactone (PCL), Poly(lactic-co-glycolic acid) (PLGA), Bionate, Chronoflex, Polyvinylidene fluoride (PVDF), Nylon 6, Cellulose, Tecothane, and Styrene Isoprene Butadiene.

In Example 6, the method of any of Examples 3-5, wherein removing the scaffold from the medical device comprises dissolving the degradable material through the porous coating.

In Example 7, the method of Example 6, wherein dissolving the degradable material through the porous coating comprises applying at least one of Dimethylacetamide (DMAC), Lutidene, Acetone, Tetrahydrofuran (THF), Toluene, Xylene, Heptane, and water to dissolve the degradable material through the porous coating.

In Example 8, the method of Example 1, wherein forming the scaffold comprises freezing water along the exterior surface of the medical device to form an ice structure thereon.

In Example 9, the method of Example 8, wherein removing the scaffold from the medical device occurs concurrently with electrospinning the polymer to apply the porous coating on the scaffold.

In Example 10, the method of any of Examples 1-9, wherein forming the scaffold comprises forming a conductive structure along the exterior surface of the medical device.

In Example 11, the method of Example 10, wherein electrospinning the polymer comprises attracting the polymer to the conductive structure of the scaffold.

In Example 12, the method of any of Examples 1-11, further comprising creating a mold having a shape, and wherein forming the scaffold comprises forming the scaffold within the mold along the exterior surface of the medical device.

In Example 13, the method of any of Examples 1-12, wherein forming the scaffold comprises forming the scaffold along a portion of the exterior surface of the medical device, and electrospinning the polymer comprises forming the porous coating adjacent the portion of the exterior surface of the medical device upon which the scaffold is formed.

In Example 14, the method of any of Examples 1-13, wherein forming the scaffold comprises forming the scaffold evenly across the exterior surface of the medical device.

In Example 15, the method of any of Examples 1-14, wherein removing the scaffold from the medical device comprises applying at least one of heat, water, and sonication to the scaffold.

In Example 16, a method of forming a porous coating on a medical device, the method comprising: forming a scaffold along an exterior surface of the medical device to support and form a pattern for the porous coating during application thereof; electrospinning a polymer to apply the porous coating in the pattern of the scaffold; and removing the scaffold from the medical device while maintaining the porous coating on the medical device.

In Example 17, the method of Example 16, wherein removing the scaffold from the medical device comprises dissolving the scaffold through the porous coating.

In Example 18, the method of Example 16, wherein forming the scaffold comprises applying a degradable material on the pattern along the exterior surface of the medical device.

In Example 19, the method of Example 18, wherein applying the degradable material comprises applying at least one of a degradable polymer on the pattern along the exterior surface of the medical device.

In Example 20, the method of Example 19, wherein applying the degradable material comprises applying at least one of a cellulose plant-based polymer, vinyl-based polymer, acrylic-based polymer, and a water-soluble polysaccharide.

In Example 21, the method of Example 20, wherein applying the degradable material comprises applying at least one of Polyethylene glycol (PEG), Polyvinyl Pyrrolidone (PVP), polyacrylamide, Polyisobutylene polyurethane (PIB PUR), Polycaprolactone (PCL), Poly(lactic-co-glycolic acid) (PLGA), Bionate, Chronoflex, Polyvinylidene fluoride (PVDF), Nylon 6, Cellulose, Tecothane, and Styrene Isoprene Butadiene.

In Example 22, the method of Example 21, wherein removing the scaffold comprises dissolving the degradable material through the porous coating by applying at least one of Dimethylacetamide (DMAC), Lutidene, Acetone, Tetrahydrofuran (THF), Toluene, Xylene, Heptane, and water to dissolve the degradable material through the porous coating.

In Example 23, the method of Example 16, wherein forming the scaffold comprises freezing water along the exterior surface of the medical device in the pattern to form an ice structure thereon.

In Example 24, the method of Example 23, wherein removing the scaffold from the medical device occurs comprises melting the ice structure, and melting the ice structure occurs concurrently with electrospinning the polymer to apply the porous coating on the scaffold.

In Example 25, the method of Example 16, wherein removing the scaffold from the medical device occurs concurrently with electrospinning the polymer to apply the porous coating on the scaffold.

In Example 26, the method of Example 16, wherein forming the scaffold comprises forming a conductive structure along the exterior surface of the medical device.

In Example 27, the method of Example 26, wherein electrospinning the polymer comprises attracting the polymer to the conductive structure of the scaffold.

In Example 28, the method of Example 16, further comprising creating a mold having a shape of the pattern, and wherein forming the scaffold comprises forming the scaffold within the mold along the exterior surface of the medical device.

In Example 29, the method of Example 16, wherein forming the scaffold includes dissolving a polymer in water to form a polymer-water combination, evaporating the water from the polymer-water combination to form a film, arranging the film on the medical device and adhering the film thereto to form the scaffold.

In Example 30, a method of forming a porous coating on a medical device, the method comprising: creating a mold having a shape; forming a scaffold in the shape of the mold along an exterior surface of the medical device to support the porous coating during application thereof; electrospinning a polymer to apply the porous coating in the pattern of the scaffold; and removing the scaffold from the medical device while maintaining the porous coating on the medical device.

In Example 31, the method of Example 29, wherein creating the mold comprises forming at least one of silicone, urethane, and an epoxy-based polymer into a structure including an interior portion having the shape.

In Example 31, the method of Example 29, wherein forming the scaffold comprises arranging the medical device within an interior portion of the mold, adding water to the interior portion of the mold, and freezing the water to form the scaffold.

In Example 33, the method of Example 29, wherein forming the scaffold includes dissolving a polymer in water to form a polymer-water combination, evaporating the water from the polymer-water combination to form a film, arranging the film on the medical device and adhering the film thereto to form the scaffold.

In Example 34, an apparatus comprising: a medical device; a degradable scaffold arranged on an exterior surface of the medical device configured to temporarily support an electrospun polymer coating; and an fibrous matrix arranged on the degradable scaffold and comprising the electrospun polymer coating.

In Example 35, the apparatus of Example 34, wherein the degradable scaffold comprises at least one of ice, Polyethylene glycol (PEG), Polyvinyl Pyrrolidone (PVP), polyacrylamide, Polyisobutylene polyurethane (PIB PUR), Polycaprolactone (PCL), Poly(lactic-co-glycolic acid) (PLGA), Bionate, Chronoflex, Polyvinylidene fluoride (PVDF), Nylon 6, Cellulose, Tecothane, and Styrene Isoprene Butadiene.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

Figure 1:
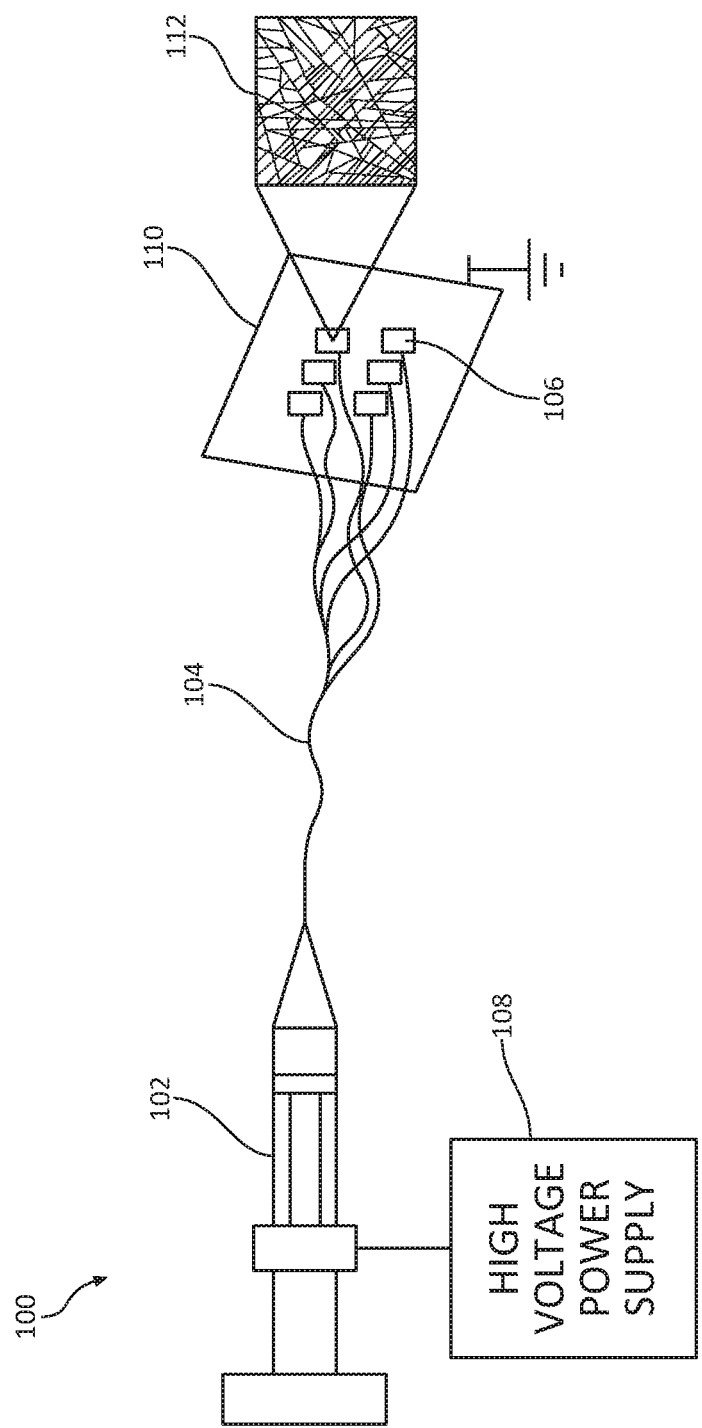
FIG. 1 is a schematic illustration of an electrospinning system in accordance with various aspects of the present disclosure.

While the disclosed subject matter is amenable to various modifications and alternative forms, specific embodiments have been shown by way of example in the drawings and are described in detail below. The intention, however, is not to limit the disclosure to the particular embodiments described. On the contrary, the disclosure is intended to cover all modifications, equivalents, and alternatives falling within the scope of the disclosed subject matter as characterized by the appended claims.

As the terms are used herein with respect to ranges of measurements (such as those disclosed immediately above), "about" and "approximately" may be used, interchangeably, to refer to a measurement that includes the stated measurement and that also includes any measurements that are reasonably close to the stated measurement, but that may differ by a reasonably small amount such as will be understood, and readily ascertained, by individuals having ordinary skill in the relevant arts to be attributable to measurement error, differences in measurement and/or manufacturing equipment calibration, human error in reading and/or setting measurements, adjustments made to optimize performance and/or structural parameters in view of differences in measurements associated with other components, particular implementation scenarios, imprecise adjustment and/or manipulation of objects by a person or machine, and/or the like.

Although the term "block" may be used herein to connote different elements illustratively employed, the term should not be interpreted as implying any requirement of, or particular order among or between, various blocks disclosed herein. Similarly, although illustrative methods may be represented by one or more drawings (e.g., flow diagrams, communication flows, etc.), the drawings should not be interpreted as implying any requirement of, or particular order among or between, various steps disclosed herein. However, certain embodiments may require certain steps and/or certain orders between certain steps, as may be explicitly described herein and/or as may be understood from the nature of the steps themselves (e.g., the performance of some steps may depend on the outcome of a previous step). Additionally, a "set," "subset," or "group" of items (e.g., inputs, algorithms, data values, etc.) may include one or more items, and, similarly, a subset or subgroup of items may include one or more items. A "plurality" means more than one.

DETAILED DESCRIPTION

FIG. 1 is a schematic illustration of an electrospinning system 100 in accordance with various aspects of the present disclosure. The electrospinning system 100 may include an application source 102 such as polymer filled syringe (with the rate of delivery between 0.1 mL/min to 10 mL/min depending on manifold and polymer) attached to a moving single nozzle, multi-nozzle manifold, or coaxial nozzle. The application source 102 may distribute a polymer solution 104 that forms the electrospun coating. In certain instances, the application source 102 may coat one or more medical devices 106 during a single application of the electrospinning process. The application source 102 may spray or sputter coat the medical devices 106.

In certain instances, an electric field may be used to draw the polymer solution 104 from the application source 102 toward the medical devices 106. A high voltage power supply 108 may be used to power the electrospinning process. The high voltage power supply 108 (e.g., with a voltage range that may be between 5,000 Volts to 30,000 Volts), for example, may be coupled to the application source 102, and a station 110, where the medical devices 106 are located, may be grounded or charged. An electric field may be created between the application source 102 and the station 110, which draws the polymer solution 104 toward the medical devices 106. The polymer solution 104 coats the medical devices 106 and, upon drying, a porous coating 112 may be formed thereon.

The polymer solution 104 (e.g., an electrospinning solution) may be a combination of a polymer or polymer blend and solvent. In certain instances, the electrospinning solution has a polymer concentration of between about 1 wt % and about 40 wt %. Suitable solvents include dimethylformamide, dimethylacetamide, N-methyl-2-pyrrolidone, dimethyl sulfoxide, acetone, cyclohexane tetrahydrofuran as well as mixtures and co-solvents thereof.

Figure 2:
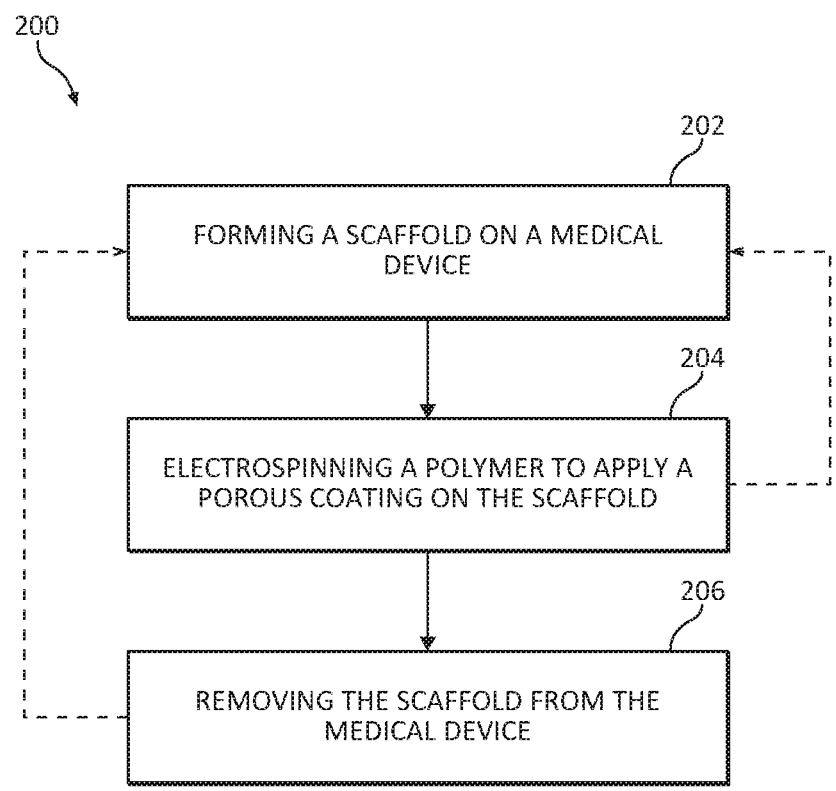
FIG. 2 is a flowchart of an example method of forming a porous coating on a medical device in accordance with various aspects of the present disclosure.

FIG. 2 is a flowchart 200 of an example method of forming a porous coating on a medical device in accordance with various aspects of the present disclosure. As shown at block 202, the method may include a step of forming a scaffold along an exterior surface of the medical device to support the porous coating during application thereof. The scaffold may be a structure onto which a porous coating (e.g., an electrospun material) may be applied. The scaffold may be arranged on the medical device to support and provide a pattern or guide for application of the porous coating. The scaffold may also protect the medical device from damage during the process as the porous coating may damage certain medical devices. The medical device may be a lead, a catheter, a balloon (porous or non-porous), a stent or stent-like device, valve, antimicrobial pouch or pouch for growing cells/incorporating cells, or other medical device. The scaffold may be applied via an application source (e.g., as described above with reference to FIG. 1).

In certain instances, forming the scaffold may include applying a degradable material along the exterior surface of the medical device. The scaffold may be degradable such that the scaffold is a temporary structure that is configured to support and/or a guide for the application of the porous coating on the medical device, and which may be removed thereafter. In certain instances, applying the degradable material may include applying a degradable polymer and/or ice along the exterior surface of the medical device. In instances where the degradable polymer is applied, applying the degradable material may include applying at least one of a cellulose plant-based polymer, vinyl-based polymer, acrylic-based polymer, and a water-soluble polysaccharide. The degradable material may be formed by dissolving a polymer in water to form a polymer-water combination.

Figure 4:
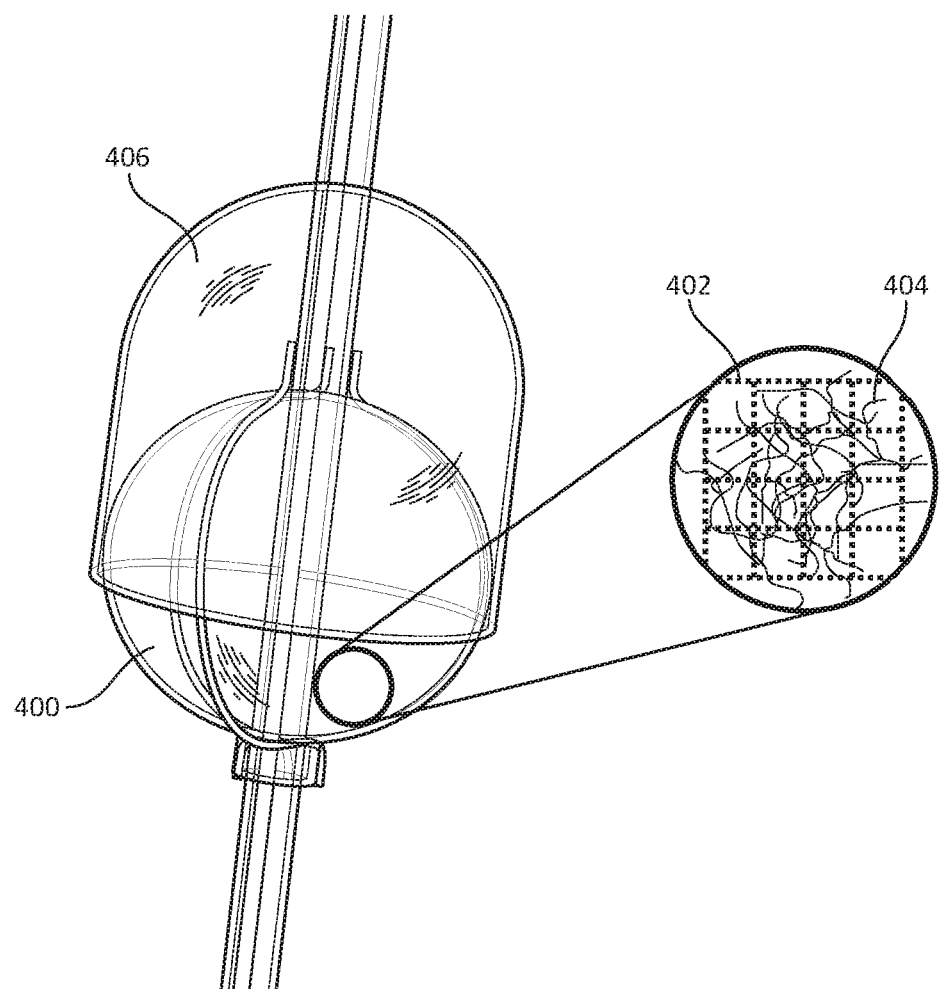
FIG. 4 is an example medical device and degradable scaffold in accordance with various aspects of the present disclosure.

In certain instances, the polymer may be concentrated by evaporating the water from the polymer-water combination to form a film. The film may be arranged on the medical device, and the film may be attached (adhering by using water droplets on the edges of the film) to form the scaffold on the medical device. The degradable material may be one or more of Polyethylene glycol (PEG), Polyvinyl Pyrrolidone (PVP), polyacrylamide, Polyisobutylene polyurethane (PIB PUR), Polycaprolactone (PCL), Poly(lactic-co-glycolic acid) (PLGA), Bionate, Chronoflex, Polyvinylidene fluoride (PVDF), Nylon 6, Cellulose, Tecothane, and Styrene Isoprene Butadiene. The polymer-based scaffold may be conductive and may provide a pattern or guide for the porous coating. An example polymer-based scaffold is shown in FIG. 4.

Figure 5:
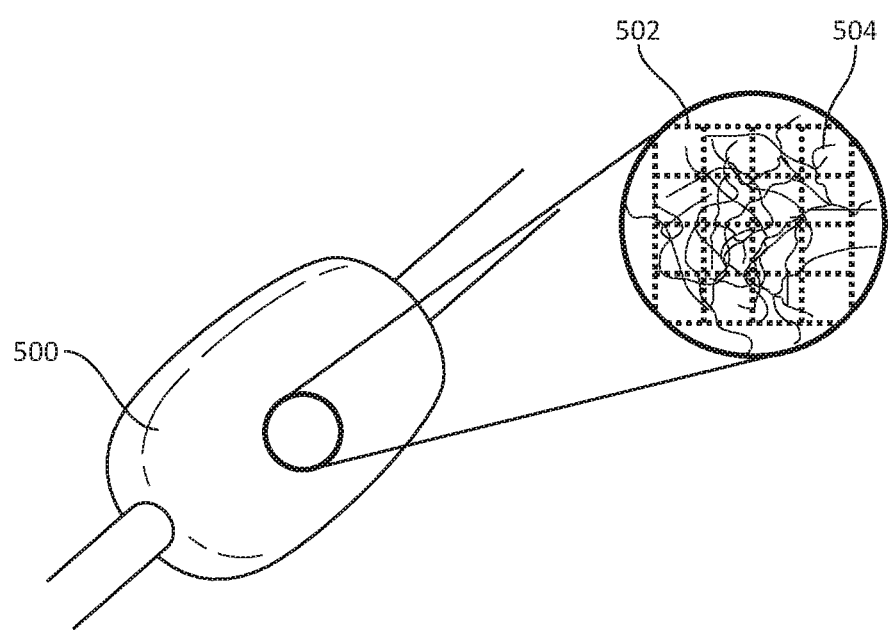
FIG. 5 is another example medical device and degradable scaffold in accordance with various aspects of the present disclosure.

Forming the scaffold on the exterior surface of the medical device, may include freezing water along the exterior surface of the medical device to form an ice structure thereon. The ice scaffold may be conductive and may provide a pattern or guide for the porous coating. An example ice-based scaffold is shown in FIG. 5.

The scaffold may be formed along a portion of the exterior surface of the medical device or the scaffold may be formed along the entirety of the medical device. As described in further detail below, the porous coating may be formed by only on portions of the medical device where the scaffold is located. The porous coating may be formed, using an electrospinning process, over only portions of the medical device where the scaffold is located.

As is shown at block 204, the method of forming the porous coating on the medical device may include electrospinning a polymer to apply the porous coating on the scaffold. During the electrospinning process, the scaffold may be a temporary structure that is configured to support and/or a guide for the application of the porous coating on the medical device. In addition and as noted above with reference to FIG. 1, the electrospinning process may use an electric field. Further, in certain instances, the scaffold may be a conductive structure that is formed along the exterior surface of the medical device. Due to the electric field applied during the electrospinning process and the conductive nature of the scaffold, the scaffold may be a conductive surface that attracts the porous coating thereto. In certain instances, the method may include attracting the porous coating (applied via the electrospinning process) to the scaffold. As a result, the scaffold may allow for gapless and uniform coating of the medical device with a desired shape and size for the porous coating.

In addition to being conductive, the scaffold may allow flow rates therethrough. In certain instances, the scaffold may be applied (e.g., using an electrospinning process similar to the porous coating) to retain a viscosity of the material whether the scaffold is ice-based or polymer-based. Maintaining the viscosity of the scaffold may protect the medical device to which it is applied. The scaffold may hold its shape during electrospinning of the porous coating and attract the polymer therein to protect the medical device.

As is shown at block 206, removing the scaffold from the medical device while maintaining the porous coating on the medical device. In certain instances removing the scaffold from the medical device may include applying at least one of heat, water, and sonication to the scaffold. In certain instances, the scaffold may be degradable such that the scaffold may degrade or dissolve in response to the application of heat, water, and sonication. As noted above, the polymer-based scaffolds may be dissolved in water for the application of a film to the medical device. Thus, the polymer-based scaffolds may be water soluble. Water applied through the porous coating may dissolve or degrade the polymer-based scaffold without disrupting the electrospun porous coating. Applying sonication or heat may also dissolve or degrade the polymer-based scaffold in certain instances. In instances where the scaffold is ice-based, sonication, heat, or water may melt the ice-based scaffold without disrupting the electrospun porous coating.

In certain instances, the solvents may be used in dissolving the degradable material through the porous coating. Dissolving the degradable material may include applying at least one of Dimethylacetamide (DMAC), Lutidene, Acetone, Tetrahydrofuran (THF), Toluene, Xylene, Heptane, and water to dissolve the degradable material through the porous coating. The solvents are applied through the pores or the porous coating without disrupting, degrading, or destroying the electrospun porous coating. Certain ones of the solvents may dissolve or degrade various ones of the above mentioned degradable materials (the scaffold materials). In addition, the solvents may be diluted, in certain instances, to avoid dissolving or degrading the electrospun porous coating and/or the medical device.

Removing the scaffold from the medical device may occur concurrently with electrospinning the polymer to apply the porous coating on the scaffold. Once the porous coating has a thickness that is able to support additional layer of the polymer, the scaffold may be removed. The scaffold may be removed using sonication, solvents, water, or heat during the electrospinning process without disrupting, degrading, or destroying the electrospun porous coating. When an ice-based scaffold is used, for example, the electrospinning process itself may generate heat which is sufficient to melt the ice structure of the scaffold concurrently with electrospinning the polymer to apply the porous coating on the scaffold. In certain instances, the ice-based scaffold may stay frozen during electrospinning the polymer. After an initial shape of the porous coating is formed with the electrospun porous coating, the porous coating will hold water, which may be sued to remove the scaffold. The water may leak out of the porous coating because the pressure of the water used to remove the scaffold may be lower than that required to push out of the electrospun porous coating. In certain instances, the electrospun porous coating may be applied to a catheter. The catheter may include a port, under the electrospun porous coating, through which the water may be removed. In instances where the electrospun porous coating is applied to a balloon, maintaining water along the surface of the balloon during electrospinning provides additional structure for the electrospun porous coating, which mitigates against shrinking of the balloon during electrospinning. For stents or other devices having more structure as compared to a balloon, the water may be removed completely during electrospinning. In certain instances, isopropyl alcohol (IPA) may be used to facilitate removal of the water.

In certain instances, the method may include forming the scaffold and electrospinning a polymer more than one time. In certain instances, the scaffold may also be removed prior to an additional iteration of forming the scaffold and electrospinning a polymer. The steps of forming the scaffold and electrospinning may be repeated in order to form multiple and/or distinct layers of the porous coating. Different polymer or polymer blends may be applied in each iteration of forming the scaffold and electrospinning and/or the scaffold and the porous coating may be formed in different patterns or locations with respect to the medical device in each iteration of forming the scaffold and electrospinning. Distinct porous coating, based on different polymer blends, may have different durometers or different properties. In this manner, the medical device may be include multiple layers of the porous coating, distinct layers of the porous coating, and/or porous coatings over different portions of the medical device.

The illustrative components shown in FIG. 2 are not intended to suggest any limitation as to the scope of use or functionality of embodiments of the disclosed subject matter. Neither should the illustrative components be interpreted as having any dependency or requirement related to any single component or combination of components illustrated therein. Additionally, any one or more of the components depicted in any of the FIG. 2 may be, in embodiments, integrated with various other components depicted therein (and/or components not illustrated), all of which are considered to be within the ambit of the disclosed subject matter. For example, the method of forming a porous coating on a medical device, described with reference to FIG. 2, may include forming a mold for a scaffold as described below with reference to FIG. 3.

Figure 3:
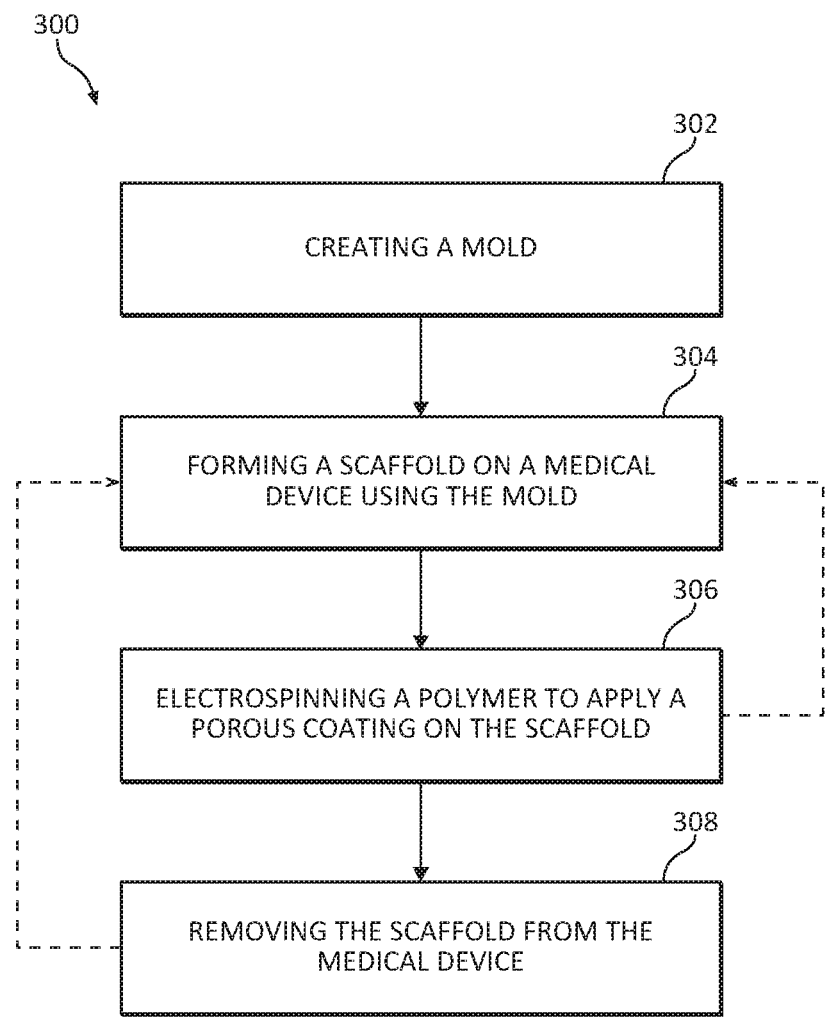
FIG. 3 is a flowchart of another example method of forming a porous coating on a medical device in accordance with various aspects of the present disclosure.

FIG. 3 is a flowchart 300 of another example method of forming a porous coating on a medical device in accordance with various aspects of the present disclosure. As shown at block 302, the method may include creating a mold having a shape. The mold may be created by forming silicone, urethane, an epoxy-based polymer, or a blend thereof into a structure including an interior portion having the shape. In certain instances, the material may be formed using Stereolithography (SLA). The mold may be formed in any desired shape that will be used for applying a scaffold to the medical device, and electrospinning a polymer on the scaffold. In addition, the mold may be formed such that the scaffold will be uniform across an exterior surface of the medical device, or the mold may be formed such that the scaffold may be formed across portions of the exterior surface of the medical device (e.g., as shown with reference to FIG. 5).

As shown at block 304, the method may include a step of forming a forming a scaffold in the shape of the mold along an exterior surface of the medical device to support the porous coating during application thereof. In certain instances, forming the scaffold may include arranging the medical device within an interior portion of the mold. Once the medical device is arranged therein, material for the scaffold may be arranged within the mold to form the scaffold in the shape of the mold.

In certain instances, forming the scaffold may include applying a degradable material along the exterior surface of the medical device and within the mold. The scaffold may be a temporary structure that is configured to support and/or a guide for the application of the porous coating on the medical device. In certain instances, applying the degradable material may include applying a degradable polymer and/or ice along the exterior surface of the medical device.

In certain instances, the polymer may be concentrated by evaporating the water from the polymer-water combination and arranged within the mold to settle on the medical devices. In other instances, the polymer may be concentrated by evaporating the water from the polymer-water combination to form a film. The film may be arranged on the medical device (within the mold), and the film may be attached to form the scaffold on the medical device. The degradable material may be one or a combination of a cellulose plant-based polymer, vinyl-based polymer, acrylic-based polymer, and a water-soluble polysaccharide, Polyethylene glycol (PEG), Polyvinyl Pyrrolidone (PVP), polyacrylamide, Polyisobutylene polyurethane (PIB PUR), Polycaprolactone (PCL), Poly(lactic-co-glycolic acid) (PLGA), Bionate, Chronoflex, Polyvinylidene fluoride (PVDF), Nylon 6, Cellulose, Tecothane, and Styrene Isoprene Butadiene. The polymer-based scaffold may be conductive and may provide a pattern or guide for the porous coating.

Forming the scaffold on the exterior surface of the medical device, may include freezing water along the exterior surface of the medical device within the mold to form an ice structure thereon. This may include adding water to the interior portion of the mold, and freezing the water to form the scaffold. The ice scaffold may be conductive and may provide a pattern or guide for the porous coating.

As is shown at block 306, the method of forming the porous coating on the medical device may include electrospinning a polymer to apply the porous coating in the pattern of the scaffold. The scaffold may be a structure onto which a porous coating (e.g., an electrospun material) may be applied. The scaffold may be arranged on the medical device to support and provide a pattern or guide for application of the porous coating. The scaffold may also protect the medical device from damage during the process as the porous coating may damage certain medical devices. The medical device may be a lead, a catheter, a balloon (porous or non-porous), a stent or stent-like device, valve, antimicrobial pouch or pouch for growing cells/incorporating cells, or other medical devices. The scaffold may be applied via an application source (e.g., as described above with reference to FIG. 1).

During the electrospinning process, the scaffold may be a temporary structure that is configured to support and/or a guide for the application of the porous coating on the medical device. In addition and as noted above with reference to FIG. 1, the electrospinning process may use an electric field. Further, in certain instances, the scaffold may be a conductive structure that is formed along the exterior surface of the medical device. Due to the electric field applied during the electrospinning process and the conductive nature of the scaffold, the scaffold may be a conductive surface that attracts the porous coating thereto. In certain instances, the method may include attracting the porous coating (applied via the electrospinning process) to the scaffold. As a result, the scaffold may allow for gapless and uniform coating of the medical device with a desired shape and size for the porous coating.

As is shown at block 308, removing the scaffold from the medical device while maintaining the porous coating on the medical device. In certain instances removing the scaffold from the medical device may include applying at least one of heat, water, and sonication to the scaffold. In certain instances, the scaffold may degrade or dissolve in response to the application of heat, water, and sonication. As noted above, the polymer-based scaffolds may be dissolved in water for the application of a film to the medical device. Thus, the polymer-based scaffolds may be water soluble. Water applied through the porous coating may dissolve or degrade the polymer-based scaffold without disrupting the electrospun porous coating. Applying sonication or heat may also dissolve or degrade the polymer-based scaffold in certain instances. In instances where the scaffold is ice-based, sonication, heat, or water may melt the ice-based scaffold without disrupting the electrospun porous coating.

In certain instances, the solvents may be used in dissolving the degradable material through the porous coating. Dissolving the degradable material may include applying at least one of Dimethylacetamide (DMAC), Lutidene, Acetone, Tetrahydrofuran (THF), Toluene, Xylene, Heptane, and water to dissolve the degradable material through the porous coating. The solvents are applied through the pores or the porous coating without disrupting, degrading, or destroying the electrospun porous coating. Certain ones of the solvents may dissolve or degrade various ones of the above mentioned degradable materials (the scaffold materials). In addition, the solvents may be diluted, in certain instances, to avoid dissolving or degrading the electrospun porous coating and/or the medical device.

Removing the scaffold from the medical device may occur concurrently with electrospinning the polymer to apply the porous coating on the scaffold. Once the porous coating has a thickness that is able to support additional layer of the polymer, the scaffold may be removed. The scaffold using sonication, solvents, water, or heat during the electrospinning process without disrupting, degrading, or destroying the electrospun porous coating. When an ice-based scaffold is used, for example, the electrospinning process itself may generate heat which is sufficient to melt the ice structure of the scaffold concurrently with electrospinning the polymer to apply the porous coating on the scaffold.

In certain instances, the method may include forming the scaffold and electrospinning a polymer more than one time (e.g., as discussed in further detail with reference to FIG. 2). In certain instances, the scaffold may also be removed prior to an additional iteration of forming the scaffold and electrospinning a polymer. The steps of forming the scaffold and electrospinning may be repeated in order to form multiple and/or distinct layers of the porous coating.

FIG. 4 is an example medical device 400 and degradable scaffold 402 in accordance with various aspects of the present disclosure. As shown in FIG. 4, the medical device 400 is a balloon structure. The inset portion of FIG. 4 shows a magnified portion of the medical device 400, the degradable scaffold 402, and a fibrous matrix 404 arranged on the degradable scaffold 402 including an electrospun polymer coating. The electrospun polymer coating is formed by an electrospinning process as described above with reference to FIGS. 1-3. The degradable scaffold 402 and the fibrous matrix 404 are shown for illustrative purposes.

The degradable scaffold 402 may be arranged on an exterior surface of the medical device 400 and may be configured to temporarily support the electrospun polymer coating. After (or during) electrospinning of the electrospun polymer coating that forms the fibrous matrix 404, the degradable scaffold 402 may be dissolved, degraded, or otherwise removed from the medical device 400 through pores of the fibrous matrix 404. The removal of the degradable scaffold 402 may occur without disturbing the fibrous matrix 404 and may occur by using heat, water, and/or sonication. In certain instances and as shown in FIG. 4, the degradable scaffold 402 may be polymer-based. The degradable scaffold 402 may include one or a combination of Polyethylene glycol (PEG), Polyvinyl Pyrrolidone (PVP), polyacrylamide, Polyisobutylene polyurethane (PIB PUR), Polycaprolactone (PCL), Poly(lactic-co-glycolic acid) (PLGA), Bionate, Chronoflex, Polyvinylidene fluoride (PVDF), Nylon 6, Cellulose, Tecothane, and Styrene Isoprene Butadiene. In addition, the degradable scaffold 402 provides a pattern or guide for formation of the fibrous matrix 404. In certain instances, the fibrous matrix 404 is formed only on the degradable scaffold 402 and not on other portions of the medical device 400 where the degradable scaffold 402 is not located. In certain instances, to form the fibrous matrix 404 over only portions of the medical device 400, a coating such as silicone may be applied to the surface of the fibrous matrix 404 after the degradable scaffold 402 is removed. Portions of porous material and non-porous material may also be formed.

To form the degradable scaffold 402 and/or the fibrous matrix 404, a mold 406 may be used. The mold 406 may be created in the desired shape of the degradable scaffold 402, which is also the desired shape of the fibrous matrix 404, as described above with reference to FIG. 3. An interior portion of the mold 406 may be the desired shape of the degradable scaffold 402 and the fibrous matrix 404. The mold 406 may be arranged around the medical device 400 during formation of the degradable scaffold 402, and removed after the degradable scaffold 402 is formed thereon.

The fibrous matrix 404 may be configured to stretch in response to inflation of the balloon. In addition, the fibrous matrix 404 may be porous to allow for elution of saline or other therapeutic drugs from the balloon.

FIG. 5 is another example medical device 500 and degradable scaffold 502 in accordance with various aspects of the present disclosure. The inset portion of FIG. 5 shows a magnified portion of the medical device 500, the degradable scaffold 502, and a fibrous matrix 504 arranged thereon (the degradable scaffold 502 and the fibrous matrix 504 are shown for illustrative purposes). As shown in FIG. 5, the medical device 500 is a balloon structure and the degradable scaffold 502 is an ice-based structure. The ice-based degradable scaffold 502 may be formed using a mold as described above with reference to FIGS. 3-4.

The degradable scaffold 502 may be arranged on an exterior surface of the medical device 500 and may be configured to temporarily support the electrospun polymer coating that forms the fibrous matrix 504. After (or during) electrospinning of the electrospun polymer coating that forms the fibrous matrix 504 (e.g., formed by an electrospinning process as described above with reference to FIGS. 1-3), the degradable scaffold 502 may be melted and removed from the medical device 500 through pores of the fibrous matrix 504. The removal of the degradable scaffold 502 may occur without disturbing the fibrous matrix 504 and may occur by using heat, water, and/or sonication.

As noted above with reference to FIG. 5, the fibrous matrix 504 may be configured to stretch in response to inflation of the balloon. In addition, the fibrous matrix 504 may be porous to allow for elution of saline or other therapeutic drugs from the balloon.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the described features. Accordingly, the scope of the present invention is intended to embrace all such alternatives, modifications, and variations as fall within the scope of the claims, together with all equivalents thereof.

We claim:

1. A method of forming a porous coating on a medical device, the method comprising:
    forming a scaffold along an exterior surface of the medical device to support and form a pattern for the porous coating during application thereof by freezing water along the exterior surface of the medical device in the pattern to form an ice structure thereon;
    electrospinning a polymer to apply the porous coating in the pattern of the scaffold; and
    removing the scaffold from the medical device while maintaining the porous coating on the medical device.

2. The method of claim 1, wherein removing the scaffold from the medical device comprises dissolving the scaffold through the porous coating.

3. The method of claim 1, wherein forming the scaffold comprises applying a degradable material on the pattern along the exterior surface of the medical device.

4. The method of claim 3, wherein applying the degradable material comprises applying at least one of a degradable polymer on the pattern along the exterior surface of the medical device.

5. The method of claim 4, wherein applying the degradable material comprises applying at least one of a cellulose plant-based polymer, vinyl-based polymer, acrylic-based polymer, and a water-soluble polysaccharide.

6. The method of claim 5, wherein applying the degradable material comprises applying at least one of Polyethylene glycol (PEG), Polyvinyl Pyrrolidone (PVP), polyacrylamide, Polyisobutylene polyurethane (PIB PUR), Polycaprolactone (PCL), Poly(lactic-co-glycolic acid) (PLGA), Bionate, Chronoflex, Polyvinylidene fluoride (PVDF), Nylon 6, Cellulose, Tecothane, and Styrene Isoprene Butadiene.

7. The method of claim 6, wherein removing the scaffold comprises dissolving the degradable material through the porous coating by applying at least one of Dimethylacetamide (DMAC), Lutidene, Acetone, Tetrahydrofuran (THF), Toluene, Xylene, Heptane, and water to dissolve the degradable material through the porous coating.

8. The method of claim 1, wherein removing the scaffold from the medical device occurs comprises melting the ice structure, and melting the ice structure occurs concurrently with electrospinning the polymer to apply the porous coating on the scaffold.

9. The method of claim 1, wherein removing the scaffold from the medical device occurs concurrently with electrospinning the polymer to apply the porous coating on the scaffold.

10. The method of claim 1, wherein forming the scaffold comprises forming a conductive structure along the exterior surface of the medical device.

11. The method of claim 10, wherein electrospinning the polymer comprises attracting the polymer to the conductive structure of the scaffold.

12. The method of claim 1, further comprising creating a mold having a shape of the pattern, and wherein forming the scaffold comprises forming the scaffold within the mold along the exterior surface of the medical device.

13. The method of claim 1, wherein forming the scaffold includes dissolving a polymer in water to form a polymer-water combination, evaporating the water from the polymer-water combination to form a film, arranging the film on the medical device and adhering the film thereto to form the scaffold.

14. A method of forming a porous coating on a medical device, the method comprising:
   creating a mold having a shape;
   forming a scaffold in the shape of the mold along an exterior surface of the medical device to support the porous coating during application thereof;
   electrospinning a polymer to apply the porous coating in the pattern of the scaffold; and
   removing the scaffold from the medical device while maintaining the porous coating on the medical device.

15. The method of claim 14, wherein creating the mold comprises forming at least one of silicone, urethane, and an epoxy-based polymer into a structure including an interior portion having the shape.

16. The method of claim 14, wherein forming the scaffold comprises arranging the medical device within an interior portion of the mold, adding water to the interior portion of the mold, and freezing the water to form the scaffold.

17. The method of claim 14, wherein forming the scaffold includes dissolving a polymer in water to form a polymer-water combination, evaporating the water from the polymer-water combination to form a film, arranging the film on the medical device and adhering the film thereto to form the scaffold.

18. An apparatus comprising:
   a medical device;
   a degradable scaffold arranged on an exterior surface of the medical device configured to temporarily support an electrospun polymer coating including ice frozen along the exterior surface of the medical device in a pattern to form an ice structure thereon; and
   a fibrous matrix arranged on the degradable scaffold and comprising the electrospun polymer coating.

* * * * *